(12) United States Patent
Tanaka

(10) Patent No.: US 11,472,834 B2
(45) Date of Patent: Oct. 18, 2022

(54) PRODUCTION METHOD FOR METAL-ENCAPSULATED CAGE-LIKE PROTEIN

(71) Applicant: Nagase & Co., Ltd., Osaka (JP)

(72) Inventor: Mami Tanaka, Kobe (JP)

(73) Assignee: NAGASE & CO., LTD., Osaka (JP)

( * ) Notice: Subject to any disclaimer, the term of this patent is extended or adjusted under 35 U.S.C. 154(b) by 666 days.

(21) Appl. No.: 16/305,032

(22) PCT Filed: Jun. 26, 2017

(86) PCT No.: PCT/JP2017/023359
§ 371 (c)(1),
(2) Date: Nov. 27, 2018

(87) PCT Pub. No.: WO2018/008441
PCT Pub. Date: Jan. 11, 2018

(65) Prior Publication Data
US 2020/0317720 A1    Oct. 8, 2020

(30) Foreign Application Priority Data
Jul. 8, 2016    (JP) .............................. JP2016-135952

(51) Int. Cl.
*C07K 1/02* (2006.01)
*C07K 1/32* (2006.01)

(52) U.S. Cl.
CPC . *C07K 1/02* (2013.01); *C07K 1/32* (2013.01)

(58) Field of Classification Search
None
See application file for complete search history.

(56) References Cited

FOREIGN PATENT DOCUMENTS

| JP | 2003-113198 | 4/2003 |
| JP | 2008-194815 | 8/2008 |
| WO | 199102704 | * 7/1991 |
| WO | 2003/099708 | 12/2003 |
| WO | 2006/132050 | 12/2006 |

OTHER PUBLICATIONS

Oligosaccharide from https://www.merriam-webster.com/dictionary/oligosaccharide. 11 pages (Year: 2021).*
Auerbach, Clinical Use of Intravenous Iron: Administration, Efficacy, and Safety, Hematology Am Soc Hematol Educ Program (2010) 2010 (1): 338-347 (Year: 2010).*
Search Report and Written Opinion, dated Sep. 19, 2017, corresponding to International Application No. PCT/JP2017/023359 (filed Jun. 26, 2017), parent of the present application, 6 pp.
Theil et al. (1979) "Similarity of the Structure of Ferritin and Iron Dextran (Imferon) Determined by Extended X-ray Absorption Fine Structure Analysis," The Journal of Biological Chemistry 254(17):8132-8134.
International Preliminary Report on Patentability, dated Jan. 17, 2019, corresponding to International Application No. PCT/JP2017/023359 (filed Jun. 26, 2017), parent of the present application, 6 pp.

* cited by examiner

*Primary Examiner* — Thomas S Heard
(74) *Attorney, Agent, or Firm* — Leydig, Voit & Mayer, Ltd.

(57) ABSTRACT

The present invention provides a production method for a metal-encapsulated cage-like protein, comprising a step of introducing a metal element into a cage-like protein in the presence of a polysaccharide to produce a metal-encapsulated cage-like protein that encapsulates the metal element.

14 Claims, No Drawings
Specification includes a Sequence Listing.

PRODUCTION METHOD FOR METAL-ENCAPSULATED CAGE-LIKE PROTEIN

CROSS-REFERENCE TO RELATED APPLICATIONS

This application is a U.S. National Stage Application filed under 35 U.S.C. § 371 of International Application No. PCT/JP2017/023359, filed Jun. 26, 2017, which claims the benefit of Japanese Application No. JP 2016-135952, filed Jul. 8, 2016. Both of these applications are hereby incorporated by reference in their entireties.

TECHNICAL FIELD

The present invention relates to a production method for a metal-encapsulated cage-like protein.

Background Art

Cage-like proteins represented by ferritin have a hollow inside thereof and can store a metal element such as iron in the hollow. Cage-like proteins that encapsulate a metal element are proposed to be used for the preparation of quantum dots and expected to be applied to lasers, solar batteries, thermoelectric conversion elements, and the like.

As the method for introducing a metal element into a cage-like protein, Patent Literature 1, for example, discloses a method for introducing iron into ferritin in a buffer solution.

CITATION LIST

Patent Literature

Patent literature 1: Japanese Unexamined Patent Publication No. 2008-194815

SUMMARY OF INVENTION

Technical Problem

However, in the method described in Patent Literature 1, the introduction efficiency of iron into the inside of ferritin is not sufficiently high and a step of removing ferritin into which iron was not introduced is required, thus there is still a room for improvement from the viewpoint of industrial production.

The present invention was accomplished in view of the above circumstance and has an object to provide a production method for a metal-containing cage-like protein capable of introducing a metal element into a cage-like protein with high efficiency.

Solution to Problem

The present invention relates to a production method for a metal-encapsulated cage-like protein comprising a step of introducing a metal element into a cage-like protein in the presence of a polysaccharide to produce a metal-encapsulated cage-like protein that encapsulates the metal element. According to the production method of the present invention, a metal element can be introduced into a cage-like protein with high efficiency, and thus a metal-encapsulated cage-like protein can be efficiently produced.

The production method of the present invention enables the introduction of a metal element into a cage-like protein with high efficiency, and thus may comprise, after the step of producing a metal-encapsulated cage-like protein, a step of purifying a mixture containing the metal-encapsulated cage-like protein by gel filtration chromatography and directly condensing the obtained eluate.

The polysaccharide may be an oligosaccharide. When this constitution is provided, a metal element can be introduced into a cage-like protein with higher efficiency.

The oligosaccharide may be a disaccharide. Additionally, the disaccharide may be at least one selected from the group consisting of sucrose, trehalose, and maltose. When this constitution is provided, a metal element can be introduced into a cage-like protein with much higher efficiency.

The oligosaccharide may be a trisaccharide, a tetrasaccharide, or a pentasaccharide. When this constitution is provided, a metal element can be introduced into a cage-like protein with much higher efficiency.

The polysaccharide may be a dextrin. When this constitution is provided, a metal element can be introduced into a cage-like protein with higher efficiency.

The production method of the present invention is particularly useful for producing a metal-encapsulated cage-like protein, wherein the cage-like protein is ferritin. Additionally, the production method of the present invention is particularly useful for producing a metal-encapsulated cage-like protein, wherein the metal element is iron.

Advantageous Effects of Invention

According to the present invention, the production method for a metal-encapsulated cage-like protein capable of introducing a metal element into a cage-like protein with high efficiency is provided.

DESCRIPTION OF EMBODIMENTS

Hereinafter, preferable embodiments of the present invention are described in detail. However, the present invention is not limited to the following embodiments.

The production method for a metal-encapsulated cage-like protein of the present embodiment comprises a step of introducing a metal element into a cage-like protein in the presence of a polysaccharide to produce a metal-encapsulated cage-like protein that encapsulates the metal element.

In the present description, the metal-encapsulated cage-like protein means a cage-like protein that encapsulates a metal element.

The cage-like protein may be any protein capable of encapsulating a metal element. Examples of the cage-like protein include ferritin, Dps (DNA binding protein from starved cells), and coat proteins of viruses. Additionally, variants of cage-like proteins having the structure and functions originated from the cage-like proteins are also included in the cage-like protein of the present description.

Ferritin is a protein composed of subunits of 20 to 25 kDa and having a diameter of 8.5 to 12 nm. Ferritin includes those derived from microorganisms, animals, and plants. Examples of the microorganism-derived ferritin include ferritins derived from *helicobacter* bacteria. Examples of the animal-derived ferritin include human-derived ferritin, mouse-derived ferritin, and horse-derived ferritin. Examples of the plant-derived ferritin include soybean ferritin. In the present description, the "ferritin" means, unless otherwise stated, ferritin that does not encapsulate a metal (that is, apoferritin).

Dps is a ferritin-like protein, and examples include Dps derived from *Listeria* bacteria and Dps derived from *Sulfolobus* bacteria. Examples of the coat protein of virus include coat protein of CCMV (cowpea chlorotic mottle virus). Of these, ferritins demonstrating high stability against heat, pH, and the like are preferable.

The cage-like protein can be produced by a method known by those skilled in the art. As an example, a cage-like protein can be produced in accordance with the method described in Japanese Unexamined Patent Publication No. 2012-200242 by constructing a plasmid containing a gene encoding a cage-like protein, culturing *E. coli* as the transformant obtained by introducing the plasmid into *E. coli* to produce the cage-like protein, and purifying the produced cage-like protein. Additionally, a variant of a cage-like protein can be prepared by a typical gene engineering technique such as a site-specific mutagenesis method in which a mutation is artificially introduced into a gene encoding the cage-like protein.

The metal element to be introduced into a cage-like protein may be any metal element storable in the hollow inside the cage-like protein. In the present description, the metal element may be a metal element itself such as a metal ion, or may be a metal compound having a metal element as a constituent element (oxides, sulfides, etc.) encapsulated in a cage-like protein. The metal element may be a metal element capable of forming a divalent metal ion and examples include iron, nickel, cobalt, indium, zinc, copper, cadmium, and gold. Of these, iron having high introduction efficiency into the inside of a cage-like protein is preferable.

The polysaccharide in the present description means a sugar that is formed by dehydration-condensation among two or more monosaccharide molecules or between one or more monosaccharide molecules and one or more sugar alcohols to form glycosidic bonds to become one molecule, and the oligosaccharides to be described below in detail are included in the polysaccharide in the present description.

Examples of the polysaccharide other than oligosaccharides include dextrin, starch, and fructan. Of these, dextrin is preferable from the viewpoint that a metal element can be introduced into a cage-like protein with higher efficiency. The polysaccharides may be used singly or in combinations of two or more.

The oligosaccharide in the present description means, among sugars that is formed by dehydration-condensation among two or more monosaccharide molecules or between one or more monosaccharide molecules and one or more sugar alcohols to form glycosidic bonds which become one molecule, those having ten or less constituent monosaccharide molecules. Of the oligosaccharides, disaccharides are preferable from the viewpoint that a metal element can be introduced into a cage-like protein with higher efficiency. Examples of the disaccharide include sucrose, trehalose, maltose, and cellobiose. Of these disaccharides, sucrose, trehalose, and maltose are preferable from the viewpoint that a metal element can be introduced into a cage-like protein with much higher efficiency. Additionally, of the oligosaccharides, trisaccharides, tetrasaccharides, and pentasaccharides are preferable from the viewpoint that a metal element can be introduced into a cage-like protein with higher efficiency. Examples of the trisaccharide include maltotriose, raffinose, and maltotriitol. Examples of the tetrasaccharide include maltotetraose, stachyose, and maltotetraitol. Examples of the pentasaccharide include maltopentaose. Of these trisaccharides, tetrasaccharides, and pentasaccharides, maltotriose for the trisaccharide, maltotetraose for the tetrasaccharide, and maltopentaose for the pentasaccharide are preferable from the viewpoint that a metal element can be introduced into a cage-like protein with much higher efficiency. The oligosaccharides may be used singly or in combinations of two or more. Note that in the production method of the present embodiment, a sugar alcohol may be used in place of the oligosaccharide, or together with the oligosaccharide. In the present description, the sugar alcohol means polyhydric alcohols having 3 to 8 carbon atoms obtained by reducing the carbonyl group of a sugar. Examples of the sugar alcohol include glycerol, erythritol, xylitol, mannitol, and sorbitol.

As an example of the introduction method for a metal element, a metal element can be introduced into a cage-like protein in a solution containing a solvent, a cage-like protein, a metal source, and a polysaccharide. For the solvent, for example, water can be used. For the metal source, metal compounds capable of forming a divalent metal ion in the solvent can be used, and examples include ammonium iron(II) sulfate (($NH_4)_2Fe(SO_4)_2$), ammonium cobalt(II) sulfate (($NH_4)_2Co(SO_4)_2$) and indium sulfate.

In this step, it is preferable to adjust pH of the solution to 7 to 8 using a buffer solution. For the buffer solution, for example, a 4-(2-hydroxyethyl)-1-piperazineethanesulfonic acid (HEPES) buffer solution can be used.

In the step of introducing a metal element into a cage-like protein to produce a metal-encapsulated cage-like protein, the temperature of the mixed solution is preferably 0 to 20° C., more preferably 5 to 15° C., and the stirring time of the mixed solution is preferably 2 to 4 hours. When the temperature and time are set as described, a metal element can be introduced into a cage-like protein with higher efficiency.

Additionally, in the step of introducing a metal element into a cage-like protein to produce a metal-encapsulated cage-like protein, it is preferable to stir the mixed solution while aerating therethrough from the viewpoint that a metal element can be introduced into a cage-like protein with higher efficiency, particularly in the case of involving the oxidation reaction of the metal element. The air flow rate is preferably 0.2 to 5 vvm, more preferably 1 to 2 vvm.

The production method of the present embodiment may comprise, after the step of producing a metal-encapsulated cage-like protein, a purification step of removing salts, a metal source, and oligomers of the cage-like protein. An example of the purification step is the method of purifying a mixture containing the metal-encapsulated cage-like protein obtained in the step of producing a metal-encapsulated cage-like protein by gel filtration chromatography. Salting-out, ultrafiltration concentration, and the like may be carried out before the mixture containing the metal-encapsulated cage-like protein is purified by gel filtration chromatography to increase the purity of the metal-encapsulated cage-like protein.

The production method of the present embodiment may comprise, after the step of producing a metal-encapsulated cage-like protein, a step of removing cage-like proteins not containing the metal element. Typically, for obtaining a metal-encapsulated cage-like protein with high purity, a step of removing cage-like proteins which did not take in a metal element is needed separately in the step of introducing a metal element into a cage-like protein to produce a metal-encapsulated cage-like protein. Examples of the method for removing cage-like proteins not containing a metal element include density gradient centrifugation. On the other hand, the production method of the present embodiment enables the introduction of a metal element into a cage-like protein with high efficiency. Thus, the production method of the present embodiment may comprise, after the step of producing a metal-encapsulated cage-like protein, a step of purifying a mixture containing the metal-encapsulated cage-like protein by gel filtration chromatography and directly condensing the obtained eluate.

When the metal-encapsulated cage-like protein is an iron-encapsulated ferritin, the introduction rate of iron into ferritin is known to be closely correlated with the absorbance at 380 nm (Arch. Biochem. Biophys., 1992, 298(1), 259-264). Thus, the introduction rate of iron into ferritin can be evaluated by measuring the absorbance at 380 nm of an iron-encapsulated ferritin solution at a constant concentration.

EXAMPLES

Hereinafter, the present invention is more specifically described in reference to Examples. However, the present invention is not limited to the following Examples. In the following Examples, the ferritin which does not encapsulate iron inside thereof is called "apoferritin".

[1. Preparation of Apoferritin]

A plasmid pKL223 was prepared in accordance with the method described in Example 1 of Japanese Unexamined Patent Publication No. 2012-200242. A gene encoding the amino acid sequence of the horse-derived ferritin, "CNHB-Fer0" (SEQ ID NO: 1) described in Japanese Unexamined Patent Publication No. 2008-194815, was synthesized, and EcoRI and WSD sequence (GAATTCAGGAGGTATTAT, SEQ ID NO: 2) were added immediately upstream of the initiation codon and PstI sequence (CTGCAG) was added downstream of the termination codon. The obtained DNA fragments were digested with EcoRI and PstI and inserted in the EcoRI-PstI gap located downstream of tac promoter on the plasmid pKL223 to construct the plasmid pKLCNH-Fer0. The prepared plasmid pKLCNH-Fer0 was introduced into E. coli BL21 to obtain the transformed E. coli BL21 (pKLCNH-Fer0).

The transformed E. coli BL21 (pKLCNH-Fer0) was cultured in 10 mL of LB medium to which ampicillin was added at a final concentration of 50 μg/mL by shaking at 200 rpm for 16 to 20 hours while heating to 37° C. to prepare a seed culture. Subsequently, 5 mL of the seed culture was added to 5 L of TB medium containing lactose (2%) and culture was initiated at 37° C., an air flow rate of 1 vvm, and a rotation speed of 290 rpm. 24 to 48 hours later, the cells were collected from the culture by centrifugation (8000×g, 15 minutes, 20° C.). The cells were suspended in 500 mL of a 50 mM tris hydroxymethyl aminomethane hydrochloride (Tris-HCl) buffer solution (pH 8.0) and collected again by centrifugation to prepare washed cells.

The washed cells were suspended again in a 50 mM Tris-HCl buffer solution (pH 8.0) in a weight of 5 times the wet weight of the cells and disrupted using a sonicator. The suspension containing the disrupted cells was centrifuged (10000×g, 15 minutes, 4° C.) and the supernatant was collected. Subsequently, the collected supernatant was heated at 70° C. for 20 minutes. The resultant was allowed to stand at room temperature for 1 hour, then centrifuged (10000×g, 15 minutes, 4° C.), and the supernatant was collected to obtain an apoferritin solution. The quantitative determination of the protein concentration of the obtained apoferritin solution was carried out by Bradford method (Quick Start protein assay).

[2. Introduction of Iron into Apoferritin]

In the present Example, an 80 mL of a solution in total was prepared in accordance with the following procedure in such a way that the final composition at the time of mixing all the components was as follows:

80 mM HEPES (pH 7.5)
0.5 mg/mL apoferritin
5 mM ammonium iron(II) sulfate
20% (w/v) disaccharide (Example 1: sucrose, Example 2: trehalose, Example 3: maltose),
to introduce iron into apoferritin.

The method in Example 1 to which sucrose was added is described below for the sake of convenience, but in Examples 2 and 3 the same method was carried out as in Example 1 with an exception of using trehalose and maltose, respectively, in place of sucrose and in Comparative Example 1 the same method was carried out as in Example 1 with an exception of not adding a disaccharide.

A mixed solution of a 500 mM HEPES buffer solution (pH 7.5) (12.8 mL), distilled water (24.7 mL), and a 50% (w/v) sucrose aqueous solution (32 mL) was prepared. The obtained solution was replaced with nitrogen and stirred at 10 to 15° C. for 20 minutes (stirring speed: 100 to 200 rpm). The 15.9 mg/mL apoferritin solution (2.5 mL) prepared in accordance with the above method was added to this solution; subsequently 8 mL of a 50 mM ammonium iron(II) sulfate aqueous solution was slowly added thereto with aeration (1 to 2 vvm) over a period of 25 minutes and stirred at 10 to 15° C. for 2 to 4 hours.

The obtained solution was centrifuged (15000×g, 15 minutes, 20° C.) and the supernatant was collected. To the collected supernatant, a 5 M sodium chloride aqueous solution in 1/10 the volume of the supernatant was added and the resultant was centrifuged (10000×g, 10 minutes, 4° C.) to collect the precipitate. A 50 mM Tris-HCl buffer solution (pH 8.0) (8 mL) was added to the collected precipitate and the resultant was stirred gently on a shaker at room temperature for 1 to 2 hours to dissolve the precipitate. The obtained solution was centrifuged (10000×g, 10 minutes, 20° C.) to collect the supernatant.

The collected supernatant was subjected to ultrafiltration (8000×g, 10 minutes, 20° C.) using Vivaspin 20 (molecular weight cutoff 50K, product of Sartorius) and concentrated to about 800 μL.

The concentrate was purified by gel filtration chromatography (HiPrep Sephacryl S-300 (product of GE Healthcare BioScience Corporation), eluent: 50 mM Tris-HCl buffer solution (pH 8.0)) to collect fractions that encapsulate monomers. Note that the analysis of each of the fractions obtained was carried out using HPLC under the following conditions.

Column: Agilent Bio SEC-5 500A
Column temperature: 25° C.
Mobile phase: 50 mM Tris-HCl buffer solution (pH 8.0)
Flow rate: 1.0 mL/min
Injection volume: 50 μL
Detection: 280 nm
Monomer retention time: close to 8.9 minutes The collected monomer-containing fractions were concentrated by ultrafiltration (8000×g, 5 minutes, 20° C.) using Vivaspin 20 (molecular weight cutoff 50K, product of Sartorius). The concentrate was diluted with a 2 mM Tris-HCl buffer solution (pH 8.0) and concentrated by ultrafiltration under the same conditions as above to obtain iron-encapsulated ferritin.

The quantitative determination of the protein concentration was carried out by Bradford method (Quick Start protein assay).

The introduction rate of iron was evaluated by adjusting the iron-encapsulated ferritin with a 2 mM Tris-HCl buffer solution (pH 8.0) to make 5.0 mg/mL, further diluting with a 50 mM Tris-HCl buffer solution (pH 8.0) to make 0.1 mg/mL, and measuring the absorbance at 380 nm of the diluted solution using a spectrophotometer (NanoDrop ND-1000 (product of Thermo Fisher Scientific)).
Additionally, as a positive control, an iron-encapsulated ferritin was produced in accordance with the method described in Examples (Preparations 4-2, 5, and 6) of Japanese Unexamined Patent Publication No. 2008-194815, and the introduction rate of iron was evaluated in the same method as above.

The results are shown in Table 1.

TABLE 1

|  | 380-nm Absorbance | Percentage to Comparative Example 1 absorbance (%) |
|---|---|---|
| Example 1 (sucrose) | 0.079 | 118 |
| Example 2 (trehalose) | 0.082 | 122 |
| Example 3 (maltose) | 0.079 | 118 |
| Comparative Example 1 (disaccharide not contained) | 0.067 | — |
| Example of Japanese Unexamined Patent Publication No. 2008-194815 | 0.082 | 122 |

The absorbances of the iron-encapsulated ferritins of Examples 1, 2, and 3, wherein iron was introduced into ferritin with a disaccharide added, were substantially equal to that of the positive control, thereby confirming that iron was introduced into ferritin with high efficiency. In contrast, the absorbance of the iron-encapsulated ferritin of Comparative Example 1, in which iron was introduced into ferritin in the absence of a disaccharide, was about 80% of the positive control, thereby confirming that the introduction rate of iron was apparently lower as compared to Examples 1, 2, and 3.

[3. Introduction of Iron to Apoferritin (2)]

The introduction of iron to apoferritin was carried out by the same method as in the above Example 1, with an exception of using each of the following polysaccharides shown in Table 2 in place of sucrose in the above Example 1, and the introduction rates of iron were evaluated (Examples 4 to 10). Additionally, the introduction of iron to apoferritin was carried out by the same method as in the above Example 1 with an exception of not adding a saccharide in the above Example 1, and the introduction rate of iron was evaluated (Comparative Example 2). The results are shown in Table 2.

TABLE 2

|  | 380-nm Absorbance | Percentage to Comparative Example 2 absorbance (%) |
|---|---|---|
| Example 4 (sucrose) | 0.074 | 123 |
| Example 5 (maltotriose) | 0.083 | 138 |
| Example 6 (maltotetraose) | 0.077 | 128 |
| Example 7 (maltopentaose) | 0.079 | 132 |
| Example 8 (dextrin*[1]) | 0.068 | 113 |
| Example 9 (dextrin*[2]) | 0.071 | 118 |
| Example 10 (dextrin*[3]) | 0.074 | 123 |
| Comparative Example 2 (polysaccharide not contained) | 0.060 | — |

*[1]Pinedex #4 (Average molecular weight about 990, Matsutani chemical Industry Co., Ltd.)
*[2]Pinedex #1 (Average molecular weight about 2300, Matsutani chemical Industry Co., Ltd.)
*[3]Pinedex #100 (Average molecular weight about 8500, Matsutani chemical Industry Co., Ltd.)

In Examples 4 to 10 in which iron was introduced into ferritin with a polysaccharide added, the absorbances at 380 nm increased by 13 to 38% as compared to Comparative Example 2 in which iron was introduced into ferritin in the absence of a saccharide, thereby confirming that iron was introduced into ferritin with higher efficiency.

As stated above, according to the production method of the present invention, it was demonstrated that a metal element was introduced into a cage-like protein with high efficiency.

The invention claimed is:

1. A production method for a metal-encapsulated cage-like protein, comprising:
a step of encapsulating a metal element into a hollow within the cage-like protein in the presence of a dextrin, a trisaccharide, a tetrasaccharide, a pentasaccharide or a disaccharide to produce a metal-encapsulated cage-like protein that encapsulates the metal element, wherein the step comprises
preparing a first solution containing the dextrin, the trisaccharide, the tetrasaccharide, the pentasaccharide or the disaccharide; preparing a second solution containing the cage-like protein; generating a solution mixture of the first solution containing the cage-like protein and the second solution containing the dextrin, the trisaccharide, the tetrasaccharide, the pentasaccharide or the disaccharide; and mixing the metal element and the solution mixture, thereby producing the metal-encapsulated cage-like protein.

2. The production method according to claim 1, comprising:
after producing the metal-encapsulated cage-like protein, purifying the metal-encapsulated cage-like protein by gel filtration chromatography and directly condensing the obtained eluate.

3. The production method according to claim 1, wherein encapsulating the metal element into the hollow within the cage-like protein is performed in the presence of a disaccharide.

4. The production method according to claim 3, wherein the disaccharide is at least one selected from the group consisting of sucrose, trehalose, and maltose.

5. The production method according to claim 1, wherein encapsulating the metal element into the hollow within the cage-like protein is performed in the presence of a dextrin.

6. The production method according to claim 1, wherein the cage-like protein is ferritin.

7. The production method according to claim 1, wherein the metal element is iron.

8. The production method according to claim 2, wherein encapsulating the metal element into the hollow within the cage-like protein is performed in the presence of a dextrin.

9. The production method according to claim 2, wherein encapsulating the metal element into the hollow within the cage-like protein is performed in the presence of a disaccharide.

10. The production method according to claim 9, wherein the disaccharide is at least one selected from the group consisting of sucrose, trehalose, and maltose.

11. The production method according to claim 1, wherein the metal element and the solution mixture are mixed for 2 to 4 hours.

12. The production method according to claim 1, wherein the metal element and the solution mixture are mixed at a temperature of 0 to 20° C.

13. The production method according to claim 1, wherein the metal element and the solution mixture are mixed at a pH between 7 to 8.

14. The production method according to claim 1, wherein the metal element is encapsulated within the cage-like protein with higher efficiency than in the absence of a dextrin, trisaccharide, tetrasaccharide, pentasaccharide or disaccharide.

* * * * *

SEQUENCE LISTING

```
<160> NUMBER OF SEQ ID NOS: 2

<210> SEQ ID NO 1
<211> LENGTH: 187
<212> TYPE: PRT
<213> ORGANISM: Artificial Sequence
<220> FEATURE:
<223> OTHER INFORMATION: A modified horse ferritin having amino-terminal
      methionine and twelve amino acids at amino-terminal

<400> SEQUENCE: 1

Met Asp Tyr Phe Ser Ser Pro Tyr Tyr Glu Gln Leu Phe Ser Ser Gln
1               5                   10                  15

Ile Arg Gln Asn Tyr Ser Thr Glu Val Glu Ala Ala Val Asn Arg Leu
            20                  25                  30

Val Asn Leu Tyr Leu Arg Ala Ser Tyr Thr Tyr Leu Ser Leu Gly Phe
        35                  40                  45

Tyr Phe Asp Arg Asp Asp Val Ala Leu Glu Gly Val Cys His Phe Phe
    50                  55                  60

Arg Glu Leu Ala Glu Glu Lys Arg Glu Gly Ala Glu Arg Leu Leu Lys
```

```
                65                  70                  75                  80
Met Gln Asn Gln Arg Gly Gly Arg Ala Leu Phe Gln Asp Leu Gln Lys
                    85                  90                  95

Pro Ser Gln Asp Glu Trp Gly Thr Thr Pro Asp Ala Met Lys Ala Ala
                100                 105                 110

Ile Val Leu Glu Lys Ser Leu Asn Gln Ala Leu Leu Asp Leu His Ala
                115                 120                 125

Leu Gly Ser Ala Gln Ala Asp Pro His Leu Cys Asp Phe Leu Glu Ser
            130                 135                 140

His Phe Leu Asp Glu Glu Val Lys Leu Ile Lys Lys Met Gly Asp His
145                 150                 155                 160

Leu Thr Asn Ile Gln Arg Leu Val Gly Ser Gln Ala Gly Leu Gly Glu
                165                 170                 175

Tyr Leu Phe Glu Arg Leu Thr Leu Lys His Asp
                180                 185

<210> SEQ ID NO 2
<211> LENGTH: 18
<212> TYPE: DNA
<213> ORGANISM: Artificial Sequence
<220> FEATURE:
<223> OTHER INFORMATION: EcoRI and WSD sequence

<400> SEQUENCE: 2
gaattcagga ggtattat                                                      18
```